June 17, 1947. E. S. BOERNER Plant Pat. 739
ROSE PLANT
Filed April 24, 1946
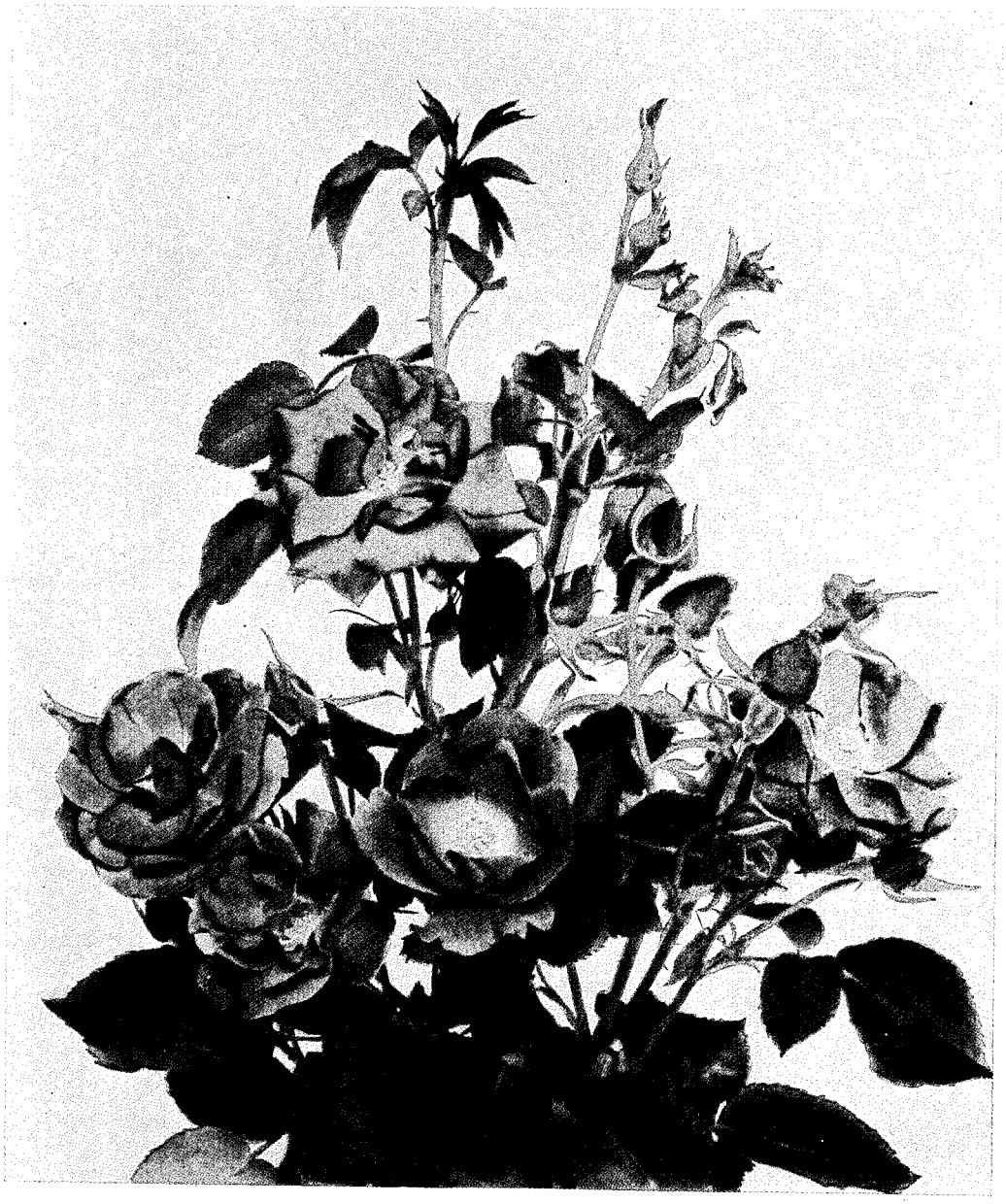
Inventor
E. S. Boerner
By Robb & Robb
Attorneys

UNITED STATES PATENT OFFICE

739

ROSE PLANT

Eugene S. Boerner, Newark, N. Y., assignor to Jackson & Perkins Company, Newark, N. Y., a corporation of New York Application April 24, 1946, Serial No. 664,525

1 Claim. (Cl. 47—61)

The present invention relates to a new and distinct variety of rose plant, originated by the crossing of two well-known Floribunda varieties "World's Fair" (Pl. Pat. 362) and "Betty Prior" (Pl. Pat. 340).

This new variety is characterized as to novelty by its extreme floriferousness, considering its low, upright and compact plant form, and the deep rich Carmine color of the flowers at opening and their Carmine overlaid with Spectrum Red coloring at the finish. At the base of the inside of the petals the color diffuses off to White which gives the effect of an eye and illuminates the flower.

Another important characteristic is the habit of the new variety of blooming continuously all through the summer season with definite resistance to burning effect of the sun, an unusual feature among roses of such dark color.

Additionally, the young foliage is of Claret Brown color which gives to the plant a constant color contrast during the summer season.

Asexual reproduction of this new variety shows the foregoing characteristics come true to form and are established.

In the drawing, a group specimen of this new variety is illustrated in detail and showing the blooms at different stages of development from bud to full blown flower, together with both young and mature foliage.

The following is a detailed description of this new variety, the color terminology being in accord with Ridgway's Color Standard:

Parentage: Seedling.
- *Seed Parent.*—"World's Fair."
- *Pollen Parent.*—"Betty Prior."

Classification:
- *Botanic.*—Large flowered polyantha.
- *Commercial.*—Floribunda.

*Flower*

(Observations made in the fields of Jackson & Perkins Company, Newark, New York, in the month of September 1945.)

Blooming habit: Recurrent—continuous.

Bud:
- *Size.*—Small.
- *Form.*—Ovoid. Is not affected by wet or hot weather.
- *Color.*—When sepals first divide—Victoria Lake, Plate I. When petals begin to unfurl—Oxblood Red, Plate I. When half blown—inside of petals—between Oxblood Red, Plate I, and Carmine, Plate I; reverse of petals—Oxblood Red, Plate I.

- *Sepals.*—Branched, "hood" above bud; curl back when petals unfurl. Color—inside—Oil Green, Plate 5; outside—Parrot Green Plate 6.
- *Calyx.*—Shape—apple. Size—small. Aspect—smooth. Odor when rubbed—none. Color—Lettuce Green, Plate 6.
- *Peduncle.*—Length—medium. Aspect—rough. Color—Lettuce Green, Plate 6. Strength—stiff; slender.
- *Opening.*—Opens up well. Is not affected by adverse conditions.

Bloom:
- *Size.*—Medium. Average size when fully expanded, 3–3½ inches.
- *Borne.*—In irregular clusters.
- *Stems.*—Medium length; normally strong.
- *Form.*—When first open—cupped. Permanence—flattens.
- *Petalage.*—Double (full but open center). Number of petals under normal conditions, 12 to 15.
- *Color.*—Center of flower—Carmine, Plate I. Outer petals—Carmine, Plate I. Base of petals (aiglet)—Naphthalene Yellow, Plate 16. Inside of petals—Carmine overlaid with Spectrum Red, Plate I; White, Plate 53, at very base of petal. Reverse of petals—Oxblood Red overlaid with Carmine, Plate I; White, Plate 53, at very base of petal. General tonality from a distance—Carmine, Plate I.
- *Discoloration.*—At end of first day—Carmine overlaid with Oxblood Red, Plate I. Second day—Carmine overlaid with Oxblood Red, Plate I. Third day—Carmine, Plate I.

Petals:
- *Texture.*—Leathery. Is not affected by wet or hot weather.
- *Appearance.*—Inside—velvety. Outside—satiny.
- *Form.*—Oval; scalloped.
- *Arrangement.*—Imbricated (regularly arranged shingle-like). Petaloids in center—few; large.
- *Persistence.*—Drop off cleanly.
- *Fragrance.*—Slight. Nature—fruity (Russet apple).
- *Lasting quality.*—On plant and as cut flower—long.

Genital organs:
- *Stamens, anthers.*—Medium size; many. Color—Orange Buff, Plate 3. Arrangement—regular around styles.

*Stamens, filaments (threads).*—Medium length. Color—Pale Lemon Yellow, Plate 4.

*Pollen.*—Buff Yellow, Plate 4.

*Styles.*—Bunched; uneven length; short; thin.

*Stigmas.*—Maize Yellow, Plate 4.

*Ovaries.*—All enclosed in calyx.

*Plant*

Form: Bush.

Growth: Medium; upright branching.

Foliage: 5 to 7 leaflets.

*Size.*—Medium.

*Quantity.*—Normal.

*Color.*—New Foliage—upper side—Claret brown, Plate I; mid-rib Parrot Green, Plate 6; under side—Maroon, Plate I. Old foliage—upper side—Dark Cress Green, Plate 31; under side—Light Hellebore Green, Plate 17.

*Shape.*—Oval pointed.

*Texture.*—Upper side—leathery; under side—smooth. Ribs and veins—ordinary.

*Edge.*—Serrated (sawtoothed).

*Serration.*—Single; large.

*Leaf stem.*—Mignonette Green, Plate 31. Under side—smooth.

*Stipules.*—Medium length; smooth.

*Disease resistance.*—Resistant.

Wood:

*New wood.*—Color—Absinthe Green, Plate 31. Bark—smooth.

*Old wood.*—Color—Cress—Green, Plate 31. Bark—smooth.

Thorns (thorns are divided into thorns, prickles, and short needles):

*Thorns.*—Quantity—on main stalks from base and on laterals from stalks—few. Form—narrow; short; downward. Color when young—Eugenia Red, Plate 13. Position—irregular.

*Prickles.*—Quantity—on main stalks and on laterals—none.

*Short needles.*—On mainstalks and on laterals—none.

I claim:

A new and distinct variety of rose plant of the Floribunda class, characterized as to novelty by its habit of prolific flowering on a low, upright, compact growth; by the coloring of its flowers both at opening and finish stages of development together with the white color of the base of the inside petals, giving the effect of an eye; by its habit of continuously blooming throughout the summer season without show of burning effect of the sun; and by the brown coloring of young foliage as constant contrasting background and for the deep color of blooms during flowering season, substantially as shown and described.

EUGENE S. BOERNER.